United States Patent [19]

Schneider-Muro

[11] Patent Number: 4,844,417
[45] Date of Patent: Jul. 4, 1989

[54] TOOL FOR REMOVING STAPLES

[76] Inventor: Karl W. Schneider-Muro, in der Breiti 13, CH-8047; Zurich, Switzerland

[21] Appl. No.: 127,481

[22] Filed: Dec. 1, 1987

Related U.S. Application Data

[63] Continuation-in-part of Ser. No. 891,280, Aug. 1, 1986, abandoned.

[51] Int. Cl.⁴ ............................................. B25C 11/00
[52] U.S. Cl. ........................................................ 254/28
[58] Field of Search ..................... 254/28, 22; 29/248, 29/267, 268; 7/3 A

[56] References Cited

U.S. PATENT DOCUMENTS

| | | | |
|---|---|---|---|
| 1,495,028 | 5/1924 | Mitchell | 254/28 |
| 1,621,576 | 3/1927 | Besancon | 29/248 |
| 2,351,703 | 6/1944 | Peterson | 254/28 |
| 3,934,286 | 1/1976 | Metzinger | 254/28 |
| 4,569,505 | 2/1986 | Braun | 254/28 |

Primary Examiner—James G. Smith
Assistant Examiner—Judy J. Hartman
Attorney, Agent, or Firm—Thomas W. Speckman; Douglas H. Pauley

[57] ABSTRACT

A tool serves for pulling staples out of a form base such as upholstered furniture, which is in the form of pliers and differs from well-known pliers by the fact that its mouth is provided with at least two pointed intersecting gripping teeth, clamping surfaces being arranged adjacent to the teeth and a tilt support in the zone of the hinge is provided.

24 Claims, 2 Drawing Sheets

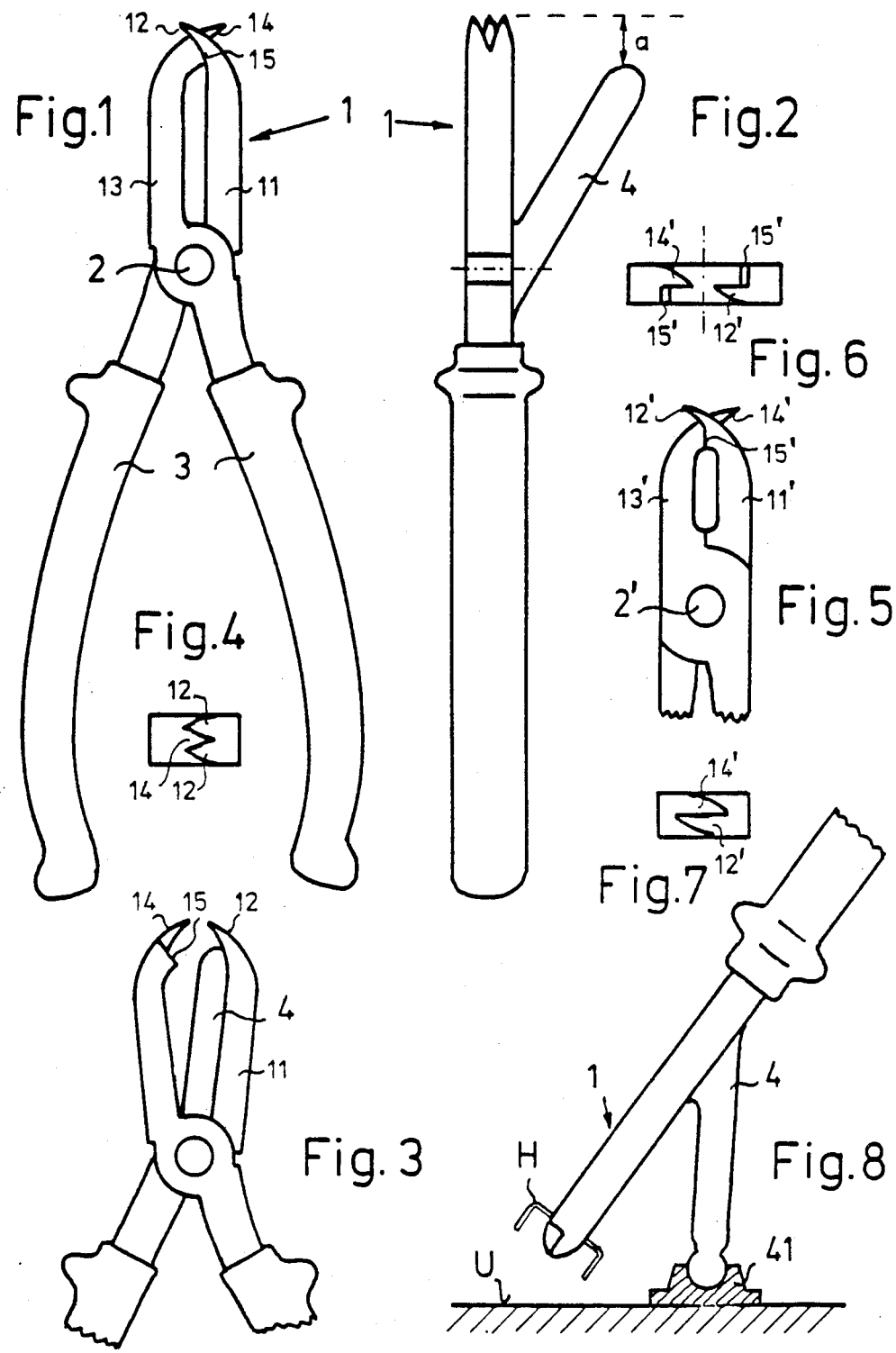

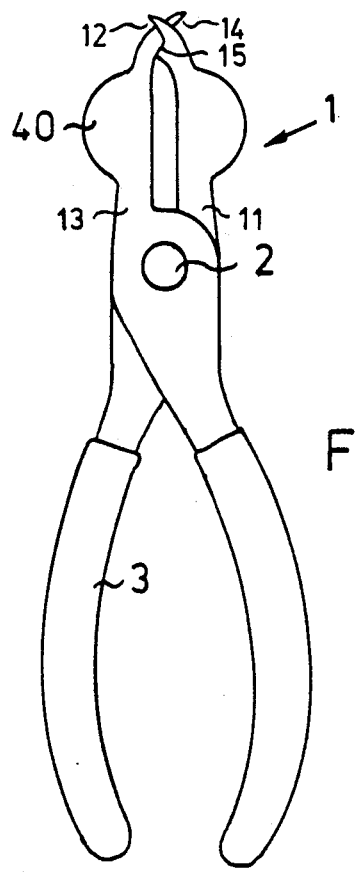
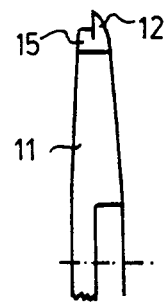
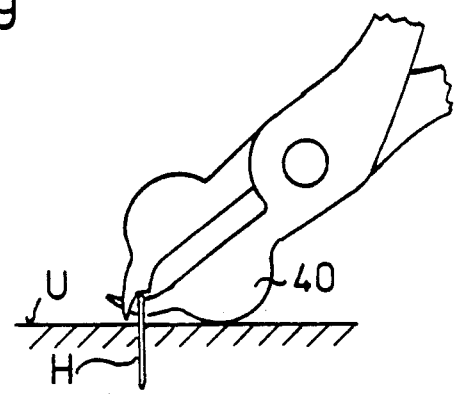
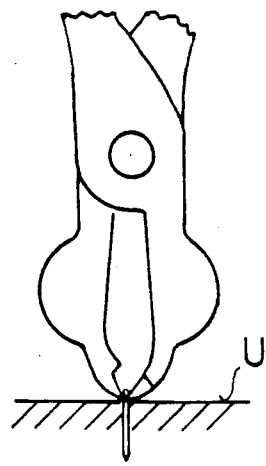
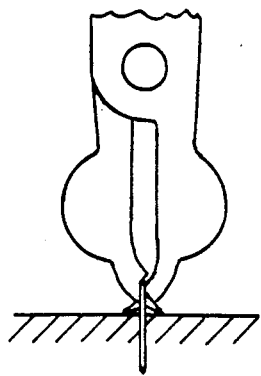
Fig. 9
Fig. 9a
Fig. 10c
Fig. 10a
Fig. 10b

TOOL FOR REMOVING STAPLES

RELATED APPLICATION

This application is a continuation-in-part of U.S. Ser. No. 891,280, filed Aug. 1, 1986, now abandoned.

BACKGROUND AND PRIOR ART

This invention relates to a tool for pulling out staples and, more particularly, staples which had been driven into a firm base such as upholstered furniture. Up to now, one used for this purpose an awl, a piercer or a screwdriver which was pushed under the staple in order to leverage it out subsequently by the same tool. In connection with this lever effect, the base was often damaged and received unsightly pressure spots which were especially disturbing if the same base was to be used again. This happens regularly with upholstered furniture if it is reupholstered. In such case, there are a large number of staples which must be carefully removed first before the new cover can be attached.

On upholstered furniture the staples are driven in or pressed in parallel to the longitudinal direction of the furniture frame. During the leveraging out by means of an auxiliary piercer or a screwdriver, this auxiliary tool is placed perpendicular to the longitudinal direction of the frame and in connection with simple leveraging, leaves behind ugly pressure marks on the edge of the frame.

Pliers for leveraging or pulling out have been known where the effect of the pliers serves merely to hold the pulled-out staple so that it will not drop to the floor. Thus, for instance EU-PS 059 778 shows a tool where one leg must be pushed under the staple which was driven in with the other leg holding the staple which was pulled out. EU-PS 0122 863 relates to a similar tool where a lever transmission is provided in which the clamping effect augments when the force for leveraging out is greater.

For office use, simple tools for pulling out staples have been known. Such a tool has two pairs of intersecting pointed gripping teeth which in the closed state are closely adjacent. Two pairs are necessary because they must bend back the bent legs of the staple perpendicular to the crossbar, viz., straighten the legs of the staple.

The aforementioned tools have the same disadvantage as an auxiliary used awl or screwdriver because the lever effect takes place perpendicular to the longitudinal axis of the staple.

SUMMARY OF THE INVENTION

The present invention relates to a tool which facilitates the aforementioned function, accelerates it and simultaneously does not damage the base.

The inventive tool operates in that, after the gripping teeth have gripped the staple, its crossbar slides upwardly along the teeth and is firmly gripped and held between the adjoining clamping surfaces. This clamping action guarantees, that both legs of the staple will be pulled out by leveraging about the tilt support.

This clamping of the staple-crossbar allows to turn the tool slightly, so that with a tool having a tilt support protruding in the swinging plane of the handles, staples can be pulled out of the frame of upholstered furniture without damaging the frame edge. Such turning is necessary if the frame is narrow. The present invention permits pulling many staples—especially on upholstered furniture—out of the frame in an efficient manner without leaving pressure tracks on the edge of the frame. The tilt support makes possible the pulling out of the staples by a tilting effect—with the support not resting on the edge of the frame but on the surface of the frame.

The plier-like tool comprises:

(a) a pair of levers pivotally connected at a point intermediate to the proximal and distal ends of said levers;

(b) handle members being adapted from the portions of said levers located proximal to said point of pivotal connection;

(c) first and second coacting pair members adapted from the portion of said levers located distal to said point of pivotal connection, said coacting jaw members having an inner side and outer side and at least one point gripping tooth that intersectingly engages the tooth of the other jaw;

(d) a tilt support that protrudes from the outer side of one jaw, said tilt support located adjacent said point of pivotal connection; and (e) a ledge-type support protrudes from the inner side of one jaw adjacent to said pointed tooth forming a clamping surface for clampingly holding a staple when gripped by said teeth.

BRIEF DESCRIPTION OF THE DRAWINGS

The invention is described in conjunction with the accompanying drawing, in which:

FIG. 1 is a front elevational view of the inventive tool;

FIG. 2 is a side elevational view;

FIG. 3 is a fragmentary front elevational view with the jaws open;

FIG. 4 is a top plan view of the gripping jaws;

FIG. 5 is a fragmentary front elevational view of a modified form of tool;

FIG. 6 is a top plan view of the modified tool with the jaws open;

FIG. 7 is a top plan view of the modified tool with the jaws closed; and

FIG. 8 is a fragmentary side elevational view of the inventive tool in operation.

FIG. 9 is a front elevational view of a modified tool of the invention;

FIG. 9a is a detail of the tool shown in FIG. 9;

FIGS. 10a–c show three phases of operation of the tool shown in FIG. 9.

DETAILED DESCRIPTION OF THE INVENTION

The tool according to FIGS. 1-4 has the form of pliers having a mouth or jaws 1, a hinge 2 and two handles 3.

However, it differs from well-known pliers by the fact that the right half jaw member 11 of the mouth has two pointed gripping teeth 12 (see FIG. 4) whereas the left half jaw member 13 of the mouth has one pointed gripping tooth 14 which enters between the teeth 12. In the closed state the teeth 12 and 14 of coacting jaw members 11 and 13 intersect as it can be seen in FIG. 1 and FIG. 4. Furthermore, the pliers have a relatively elongated tilt support or fulcrum 4 which is attached in the area of pivotal connection or hinge 2 and is angled forward. The tilt support is firmly connected or fixed with respect to the mouth part 11 and the left handle 3. It is set back on the pliers a certain distance relative to the gripping teeth.

On the left half of the mouth, on jaw member 13 there is provided a ledge type support or clamping surface 15 which is adjacent the tooth 14 (see FIG. 3) and in the closed state engages the half 11 of the mouth.

During the pulling of a staple out of the base, the staple slides along the teeth and is then held by being clamped between the surface 15 of the half 13 of the mouth and the half 11 of the mouth as is illustrated in FIG. 8.

FIG. 3 shows the pliers with the mouth open and the first and second coacting jaw members are apart. There it can be seen that the tilt support 4 swings along with the right half of the mouth on the outer side of one jaw. Since the staples have only little thickness the mouth of the pliers is nearly closed as soon as the teeth have gripped the staple and the staple is held clamped between the surface 15 and the jaw 13.

FIGS. 5–7 show the mouth of different pliers having only two pointed gripping teeth 12', 14'. The larger or base ends of these gripping teeth goes over into the clamping surface 15' of the jaws or mouth parts 11', 13'.

FIG. 8 shows these pliers in operation during the pulling of a staple H out of the base U. Here the pointed gripping teeth have first reached under the staple. As soon as the staple has been pulled out of the base, it slides backward along the pointed teeth and is held firmly between the clamping surface 15 and half or jaw 13. In order to pull out the staple, the pliers are tilted around the tilt support 4 which facilitates this work. On this tool the tilt support or fulcrum 4 on its free end is equipped with a foot 41 which enlarges the support surface during the pulling out of the staples. In this way the pressure is distributed over a larger surface and the danger of damaging a relatively soft base is decreased. The foot is flexibly connected as by a ball and socket joint with the support and for this purpose the free end of the support is made spherical. With an appropriate design, the foot can serve also as an extension of the support. This is an advantageous point for staples having relatively long sides as they normally are used in soft bases. The foot 41 can be made of metal or as a plastic extension which can be put on the tilt support. Instead of attaching the tilt support in the area of the hinge, it can also be attached on one half or jaw or two supports can be provided on both halves or jaws of the mouth. The smaller the distance is between the support and the pointed gripping teeth, the smaller is the lever arm and handle and the smaller is the force needed for leveraging out. However, this also decreases the possiblity of being able to pull out long staples entirely and safely by the mere lever effect. It is advantageous if the two legs 3 of the pliers are bent at an angle as close as possible to the hinge in the direction of the tilt support. Consequently the user has to turn the arm less around the bending angle. Furthermore, there is a better lever effect because the vertical distance between the point of attack of the pliers is farther removed from the point of support of the tilt support at the start of the tilting motion.

FIG. 9 shows pliers which differ from the pliers as described and shown in FIG. 1, in that the tilt-support 40 is arranged on the outside of the mouth parts or jaws 11, 13 and protrudes in the swinging plane of the handles 3.

FIG. 9a shows the mouth-part or jaw 11 from the inner side. Here the clamping surface 15 joining the pointed tooth 12 can be clearly seen. These pliers with its teeth 12, 14 can pull out a staple H as described before. The operation has three phases:

(a) opening the pliers, pressing them on the base and pressing the handles together, so that the teeth 12, 14 grip under the staple H (as shown in FIG. 10a)

(b) closing the pliers, so that the crossbar of the staple slides upwardly along the teeth until it is firmly gripped between the clamping surfaces 15. It is of no importance if now only one leg of the staple has been partly pulled out of the base U whilst the second leg is still held in the base (FIG. 10b)

(c) Now the closed plier can be tilted over the tilt-support 40 as shown in FIG. 10c and the staple will be pulled out of the base, even when one leg of the staple was held in the base until now.

When staples are to be pulled out of a narrow frame of upholstered furniture with these pliers it may be necessary to turn the plier slightly when it is in the position of FIG. 10b in order not to damage the edge of the frame.

While in the foregoing specification a detailed description of an embodiment of the invention has been set down for purpose of illustration, many variations in the details herein given may be made by those skilled in the art without departing from the spirit and scope of the invention.

I claim:

1. A plier-like tool for removing staples firmly set in a base, the tool comprising:

a first handle, a second handle, a hinge pin, said first handle pivotable with respect to said second handle about said hinge pin;

said first handle having a first jaw member extending beyond said hinge pin, a single pointed gripping tooth projecting outward from a first free end of said first jaw member and a first clamping surface surrounding a first base of said single pointed gripping tooth;

said second handle having a second jaw member extending beyond said hinge pin, two pointed gripping teeth projecting outward from a second free end of said second jaw member and a second clamping surface surrounding a second base of said two pointed gripping teeth;

said single pointed gripping tooth matingly engaging between said two pointed gripping teeth whereby when said first jaw member is closed relative to said second jaw member the staple slides from a pointed end of said single pointed gripping tooth and pointed ends of said two pointed gripping teeth toward said first clamping surface and said second clamping surface, in a closed position of said first jaw member relative to said second jaw member the staple being firmly clamped between said first clamping surface and said second clamping surface; and an elongated tilt support bar attached near said hinge pin to one of said first handle and said second handle, and said elongated tilt support bar extending outward from a general plane within which said first handle and said second handle pivot.

2. A plier-like tool according to claim 1 wherein said tilt support bar is angled outward from said first jaw mebber and said second jaw member and forms an acute angle with respect to said first jaw member and said second jaw member.

3. A plier-like tool according to claim 2 further comprising a flat-bottomed foot attached to a tilt support bar free end of said tilt support bar.

4. A plier-like tool according to claim 3 wherein said flat-bottomed foot is attached with a ball-in-socket joint.

5. A plier-like tool according to claim 1 further comprising a flat-bottomed foot attached to a tilt support bar free end of said tilt support bar.

6. A plier-like tool according to claim 5 wherein said flat-bottomed foot is attached with a ball-in-socket joint.

7. A plier-like tool according to claim 1 wherein said first handle and said second handle are each bent toward said tilt support bar.

8. A plier-like tool for removing staples firmly set in a base, the tool comprising:
a first handle, a second handle, a hinge pin, said first handle pivotable with respect to said second handle about said hinge pin;
said first handle having a first jaw member extending beyond said hinge pin, a first pointed gripping tooth projecting outward from a first free end of said first jaw member and a first clamping surface surrounding a first base of said first pointed gripping tooth;
said second handle having a second jaw member extending beyond said hinge pin, a second pointed gripping tooth projecting outward from a second free end of said second jaw member and a second clamping surface surrounding a second base of said second pointed gripping tooth;
said first pointed gripping tooth matingly engaging with said second pointed gripping tooth whereby when said first jaw member is closed relative to said second jaw member the staple slides from a first pointed end bf said first pointed gripping tooth and a second pointed end of said second pointed gripping tooth toward said first clamping surface and said second clamping surface, in a closed position of said first jaw member relative to said second jaw member the staple being firmly clamped between said first clamping surface and said second clamping surface; and
an elongated tilt support bar attached near said hinge pin to one of said first handle and said second handle, and said elongated tilt support bar extending outward from a general plane within which said first handle and said second handle pivot.

9. A plier-like tool according to claim 8 wherein said tilt support bar is angled outward from said first jaw member and said second jaw member and forms an acute angle with respect to said first jaw member and said second jaw member.

10. A plier-like tool according to claim 9 further comprising a flat-bottomed foot attached to a tilt support bar free end of said tilt support bar.

11. A plier-like tool according to claim 10 wherein said flat-bottomed foot is attached with a ball-in-socket joint.

12. A plier-like tool according to claim 8 further comprising a flat-bottomed foot attached to a tilt support bar free end of said tilt support bar.

13. A plier-like tool according to claim 12 wherein said flat-bottomed foot is attached with a ball-in-socket joint.

14. A plier-like tool according to claim 8 wherein said first handle and said second handle are each bent toward said tilt support bar.

15. A plier-like tool for removing staples firmly set in a base, the tool comprising:
a first handle, a second handle, a hinge pin, said first handle pivotable with respect to said second handle about said hinge pin;
said first handle having a first jaw member extending beyond said hinge pin, a first pointed gripping tooth projecting outward from a first free end of said first jaw member and a first clamping surface surrounding a first base of said first pointed gripping tooth;
said second handle having a second jaw member extending beyond said hinge pin, a second pointed gripping tooth projecting outward from a second free end of said second jaw member and a second clamping surface surrounding a second base of said second pointed gripping tooth;
said first pointed gripping tooth matingly engaging with said second pointed gripping tooth whereby when said first jaw member is closed relative to said second jaw member the staple slides from a first pointed end of said first pointed gripping tooth and a second pointed end of said second pointed gripping tooth toward said first clamping surface and said second clamping surface, in a closed position of said first jaw member relative to said second jaw member the staple being firmly clamped between said first clamping surface and said second clamping surface; and
at least one of said first jaw member and said second jaw member having a tilt-support section projecting outward into a general plane within which said first handle and said second handle pivot.

16. A plier-like tool according to claim 15 wherein said tilt-support section is a curved projection of said at least one of said first jaw member and said second jaw member.

17. In a plier-like tool, for removing staples firmly set in a base, having a first handle, a second handle, a hinge pin, said first handle pivotable with respect to said second handle about said hinge pin; said first handle having a first jaw member extending beyond said hinge pin, said second handle having a second jaw member extending beyond said hinge pin, the improvement comprising: at least one first pointed gripping tooth projecting outward from a first free end of said first jaw member and a first clamping surface surrounding a first base of said at least one first pointed gripping tooth, at least one second pointed gripping tooth projecting outward from a second free end of said second jaw member and a second clamping surface surrounding a second base of said at least one second pointed gripping tooth;
said at least one first pointed gripping tooth matingly engaging with said at least one second pointed gripping tooth whereby when said first jaw member is closed relative to said second jaw member the staple slides from a first pointed end of each of said at least one first pointed gripping tooth and a second pointed end of each of said at least one second pointed gripping tooth toward said first clamping surface and said second clamping surface, in a closed position of said first jaw member relative to said second jaw member the staple being firmly clamped between said first clamping surface and said second clamping surface; and an elongated tilt support bar attached near said hinge pin to one of said first handle and said second handle, and said elongated tilt support bar extending outward from a general plane within which said first handle and said second handle pivot.

18. A plier-like tool according to claim 17 wherein said tilt support bar is angled outward from said first jaw member and said second jaw member and forms an acute angle with respect to said first jaw member and said second jaw member.

19. A plier-like tool according to claim 18 further comprising a flat-bottomed foot attached to a tilt support bar free end of said tilt support bar.

20. A plier-like tool according to claim 19 wherein said flat-bottomed foot is attached with a ball-in-socket joint.

21. A plier-like tool according to claim 17 further comprising a flat-bottomed foot attached to a tilt support bar free end of said tilt support bar.

22. A plier-like tool according to claim 21 wherein said flat-bottomed foot is attached with a ball-in-socket joint.

23. A plier-like tool according to claim 17 wherein said first handle and said second handle are each bent toward said tilt support bar.

24. In a plier-like tool, for removing staples firmly set in a base, having a first handle, a second handle, a hinge pin, said first handle pivotable with respect to said second handle about said hinge pin; said first handle having a first jaw member extending beyond said hinge pin, said second handle having a second jaw member extending beyond said hinge pin, the improvement comprising: at least one first pointed gripping tooth projecting outward from a first free end of said first jaw member and a first clamping surface surrounding a first base of said at least one first pointed gripping tooth, at least one second pointed gripping tooth projecting outward from a second free end of said second jaw member and a second clamping surface surrounding a second base of said at least one second pointed gripping tooth;

said at least one first pointed gripping tooth matingly engaging with said at least one second pointed gripping tooth whereby when said first jaw member is closed relative to said second jaw member the staple slides from a first pointed end of each of said at least one first pointed gripping tooth and a second pointed end of each of said at least one second pointed gripping tooth toward said first clamping surface and said second clamping surface, in a closed position of said first jaw member relative to said second jaw member the staple being firmly clamped between said first clamping surface and said second clamping surface; and at least one of said first jaw member and said second jaw member having a rounded protuberance tilt-support section projecting outward into a general plane within which said first handle and said second handle pivot.

* * * * *